United States Patent [19]

Favié et al.

[11] 4,435,545

[45] Mar. 6, 1984

[54] METHOD OF PREPARING COSMETOLOGICAL POLYMERS

[75] Inventors: Claude Favié; Michel Mercadier, both of Pau, France

[73] Assignee: Societe Nationale Elf Aquitaine (Production), France

[21] Appl. No.: 317,532

[22] Filed: Nov. 2, 1981

Related U.S. Application Data

[63] Continuation of Ser. No. 93,511, Nov. 13, 1979, abandoned.

[30] Foreign Application Priority Data

Nov. 21, 1978 [FR] France .................. 78 32742
Nov. 21, 1978 [FR] France .................. 78 34743

[51] Int. Cl.$^3$ .......................... C08F 8/34; C08F 8/12; C08F 8/18; C08F 8/00
[52] U.S. Cl. ........................ 525/344; 210/688; 423/24; 525/350; 525/351; 525/353; 525/355; 525/359.4; 525/366; 525/377; 525/379; 525/382; 525/383; 525/384; 525/385; 525/386
[58] Field of Search .............. 525/344, 355, 350, 351, 525/353, 359.4, 379, 382, 366, 383, 384, 374, 385, 386, 375, 327.3

[56] References Cited

U.S. PATENT DOCUMENTS

| 2,781,335 | 2/1957 | Cupery | 526/273 |
| 2,992,210 | 7/1961 | Gluckman | 526/273 |
| 3,732,309 | 5/1973 | Garnish | 528/109 |
| 4,166,079 | 8/1979 | Tatsukami | 525/208 |

OTHER PUBLICATIONS

Chem. Abst., 80, 5023w (1974).

Primary Examiner—C. A. Henderson

[57] ABSTRACT

Novel organic polymers have a chain carrying active groups, a hydroxyl, alkoxy, halogen, thiol or sulphide group or a second active group being attached as a substituent to a carbon which is in the alpha position with respect to that carrying the first active group. The preparation of these polymers is advantageously effected using polymers carrying epoxide bridges, which are opened by the action of an active cosmetological or other active compound. These polymers are particularly suitable for the protection of the skin against solar radiation, as creams or gels for the skin and for the hair and/or as pigments.

18 Claims, No Drawings

METHOD OF PREPARING COSMETOLOGICAL POLYMERS

This is a continuation of application Ser. No. 93,511, filed Nov. 13, 1979, now abandoned.

BACKGROUND

The invention relates to organic polymers carrying active groups chemically fixed to the polymer chain, these groups having specific properties, particular examples being chromophoric, tensio-active, ion exchange, cosmetological, rheological, chelating or other groups. The invention includes the uses of polymers provided with such groups, in particular for the preparation of pigments, varnishes, paints, ion exchange resins, cosmetic products, chromatographic supports and so on.

In order to provide simplification, the following part of the present description relates mainly to cosmetic agents which illustrate the invention, but it is to be understood however that the invention is applicable to other areas of use, because the active cosmetological groups can be replaced in analogous fashion by other active groups.

For several years, there has been a tendency in cosmetology to utilize various active substances, not only as such, but also by fixing them to macromolecules. The main reason for this is that the skin tends to absorb various monomeric active compounds, which gives the disadvantage of removing a part of these compounds from the surface of the skin where their action should occur. On the other hand, penetration into the organism can be prejudicial to health in many cases. This penetration can be considerably diminished or even totally prevented, if the active substance is in the form of a polymer of sufficiently large molecular dimensions. Various polymers have thus been employed for this purpose, particularly polyacrylates, polymethacrylates and their copolymers, especially those with vinyl-pyrrolidone, the polyoxyalkylenes and so on. The important point of this technique is the manner in which the active cosmetological groups are attached to the polymer chain. This has been realised previously through the intermediary of two conjugated carboxylic groups:

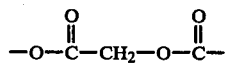

according to French Patent Specification No. 73 23704, or by means of an imide group:

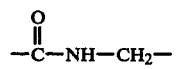

as described in French Patent Application No. 76 23174. However, this technique still needs to be perfected. It is necessary for the activity of the groups concerned not to undergo too great a reduction by reason of their combination with the polymer and that the product can exhibit the requisite solubility for its intended use.

SUMMARY

The present invention relates to an improvement in the products indicated above. In fact, it allows the formation of a chemical bond between the active groups and the macromolecule, whilst conserving good activity of the active groups. Moreover, the products according to the invention can be made soluble or insoluble, as required, in water or in organic solvents. The preferred process of preparation of the products according to the invention allows the utilization, as starting materials, of products which are easily and economically available. This process renders possible the ready fixation of the desired active molecules on the polymer chains. It also allows the convenient elimination of undesirable groups, contrary to what has occurred in processes of the prior art, particularly those which utilize anhydrides.

The invention can be applied to various types of substances, particularly to those whose role is the treatment of the hair or the protection of the skin, in particular creams, gels and ultraviolet absorbants, whether or not they are products having a decorative or hygienic character. Thus the invention is highly utilizable, for example, for the fixation of U.V. absorbants or of colourants on various polymers, the latter also comprising copolymers.

One of the important applications of the present invention concerns polymers carrying mercaptan groups. It relates more particularly to the production of mercaptan polymers, in which the —SH function is located in a chain adjacent a carboxylic group, the latter being fixed to the macromolecule of a polymer.

DESCRIPTION OF THE INVENTION

Polymercaptans are industrial products utilized in various areas, particularly for the complexing of heavy metals, with a view to their elimination in the form of mercaptides, as cross-linking agents for epoxy resins, in sealing joints, for adhesive composition, for treatment of the hair or fibres, as ion exchange resins and so on. In view of the utility of these polymers, industry has contemplated various processes of preparation, but the question of a process which is both economic and leads to interesting products still remains unanswered. In particular, a method is known which consists in reacting an aliphatic mercapto-acid with an acrylic or methacrylic copolymer carrying epoxy groups on the side chains attached to the chain of the macromolecule. However, this technique, described in U.S. Pat. No. 2,992,210, generally leads to partially cross-linked products having a very high content of thiol groups. It has also been proposed to introduce —SH groups into vinyl chains by the action of sodium hydro-sulphide on polyvinyl chloride (IWATE University, Japan), but this reaction is difficult to conduct and must be carried out in liquid ammonia.

The present invention relates to an economical process, which is easily carried out and leads to products which can readily be prevented from undergoing spontaneous cross-linking and in which the number of mercapto groups per macromolecule can be regulated as desired.

The novel products according to the invention are organic polymers, having a chain which carries one or more specific active groups fixed to the chain by chemical bonds, characterized in that each of these bonds is connected to a carbon atom adjacent to another carbon which carries a hydroxyl, alkoxy, halogen, thiol or sulphide substituent or a second active group similar to the first. Stated otherwise, the polymers according to the invention are characterized by pairs of the above-indicated substituents in the alpha position with respect to one another, one at least being a specific active group.

In a preferred form of the invention, the polymer also carries pairs of substituents in the alpha position with respect to one another, constituted by hydroxyls, halogens and/or thiols alone, i.e. without active groups.

The configuration of the polymers according to the invention can be illustrated diagrammatically by a chain:

where A designates the recurrent unit of the polymer, the groups R and R' being the substituents, defined above, attached to two adjacent carbon atoms. It will be understood that the chain can be that of a copolymer:

or

where B and C are other units, which can if required also carry the radicals RR'.

In the products according to the invention, the two adjacent carbon atoms carrying the groups RR' can be part of the polymer backbone chain itself or they can be located in its side chains. The first case corresponds to the configuration:

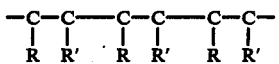

while the second can be represented by the diagram:

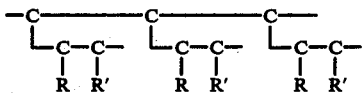

The polymer chain of a product according to the invention can be that of a polyolefin, a polyvinyl compound, a polyoxyalkylene, a polydiene, a polysaccharide and so on, if required containing a copolymer. Particularly suitable are polyacrylates, polymethacrylates, polypropylenes, polyisobutenes and so on, including copolymers, for example polyvinyl-pyrrolidone. Unsaturated oligomers derived from the propene or isobutene chain are particularly useful.

In the particular case of active cosmetological groups, these include, for example, compounds such as alicyclic dienones, cinnamic derivatives, galloyl oleates, p-amino-benzoates, benzophenone, urocanic acid, benzylidene-camphor, cyano-acrylic derivatives, salicylic compounds, various colourants and so on. As cosmetic agents are particularly well known in the art, it is not necessary to give here the formulae of these various compounds. A polymer according to the invention can also carry several active cosmetological groups of different kinds.

By way of illustration, the structure is given below of a fragment of a polyacrylic ester representing an example of a compound in which two adjacent carbon atoms are substituted in accordance with the invention, being located in the ester residue of the polymer:

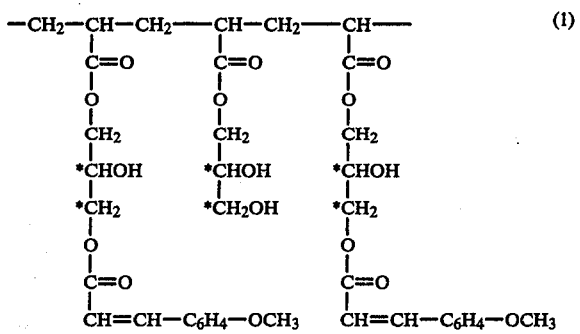

As can be seen, in the first and third side chains, of the two carbon atoms indicated by asterisks, one carries an OH (R in the formula given above), while the second carries the radical of p-methoxy cinnamic acid:

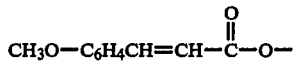

which is a specifically active cosmetological compound, in particular for the absorption of U.V. This group constitutes the radical R' of the formula indicated above. It can also be seen that, in the second side chain, the two carbons in the alpha position to one another both carry hydroxyl groups which tend to confer solubility on the macromolecule. This non-limitative example makes it understandable how, according to the invention, a more or less large proportion of the substitutions in the alpha position can be made with active cosmetological groups, while another part, carrying OH, halogen, alkoxy or SH groups, renders possible modification of certain other properties of the molecule and, in particular, its solubility. It will be understood that the ratio of 2 p-methoxy-cinnamic groups per 4 OH groups, in the example of the above formula, is in no way limitative. By varying this ratio, products of the desired properties can be obtained, particularly insoluble solids or polymers soluble in water, alcohol, glycerol and/or other solvents.

A particularly practical process of preparation of the polymers according to the invention consists in utilizing polymers carrying epoxy bridges which are opened by reaction with an active compound. The epoxide groups can be located within the actual chain of the polymer or at the ends of the chain, as is the case for example with epoxided polyisoprene or an epoxy resin oligomer. They can be located in a side chain, as is the case with glycidyl polymethacrylates or those of other alkyl groups having an epoxy function. In one case as in the other, a compound which is active, for example cosmetologically, containing reactive hydrogen atoms, is reacted with the selected epoxided polymer.

The reaction in question can be expressed as follows:

where Q represents the active cosmetological group.

This reaction according to the invention is preferably conducted in a liquid in which the polymer to be treated has been dissolved. Best yields are obtained when operating in the presence of an organic base, particularly a triamine, if the active compound is an acid. Depending upon the reactivity of the compounds present, operation is effected at a more or less elevated temperature, e.g. ranging from 20° to 150° C. and particularly from 40° to 80° C. It generally takes a time of the order of 1 to 30 hours.

As can be seen from the above, the properties of the polymer can be modified by the nature and proportion of the R and R' radicals introduced by opening the epoxy bridges. Thus, if it is possible to replace all the epoxy groups by residues of an active compound, by utilizing an appropriate proportion of the latter in the reaction with the epoxided polymer, it is preferable in general to attach groups only to part of the epoxy groups. According to a preferred form of the invention, the remaining epoxides are then opened in known manner, for instance by hydrolysis, alcoholysis or some other reaction, in order to introduce in their place OH radicals and, for example, SH, alkoxy, sulphide, amine, second OH, halogen or other groups. Thus, in the particular case of opening of the expoxided bridge with HCl, the bridges become:

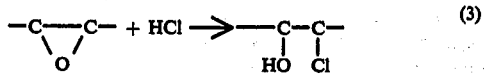
(3)

The specific active groups of the agents employed according to the invention, in the above reaction, can have one or more reactive hydrogens. When it is desired to obtain soluble polymers, it is preferable to use groups only having a single reactive hydrogen, because the presence of a second can give rise to cross-linking with a second chain of the polymer and thus yield an insoluble compound. Nevertheless, such cross-linking can be desired in certain cases and then the use of cosmetological or other agents with several reactive hydrogens becomes useful.

The case of groups with several reactive hydrogens is often met with colourants which are to be attached to the polymer, within the scope of the present invention. Such a case is constituted by colourants carrying 2—SO₃H groups, such as are present for example in various diazoic colourants derived from naphthalene. In these cases, it is desirable to block one of these sulphonic groups in known manner, in order to react only one of them with epoxy groups.

In the examples given above, the reactive hydrogen of the active cosmetological group to be attached to the polymer is derived from an acid function. This hydrogen can also be that of an amine. For this, the NH₂ function of the desired compound can react with the halogenated derivative (3) indicated above. A product is then obtained in which the part of the molecule indicated with the asterisks in formula (1) takes the form:

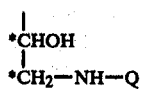
(4)

where Q represents the active group of the amine substance utilized. Thus, polymers are obtained in which the chain carries both amine groups and other active groups, as for example the p-methoxy-cinnamic groups illustrated by formula (1) above.

In the application of the invention to polymercaptans, one process consists of eliminating an electropositive or electronegative atom or group of a polymer by reaction with, respectively, an electronegative or electropositive atom or group of a compound carrying the thiol function, and is characterized in that an electropositive atom or group to be eliminated is located in the form of a carboxylate.

Stated otherwise, the process according to the invention makes use of a reaction which can be represented, in a general manner, as follows:

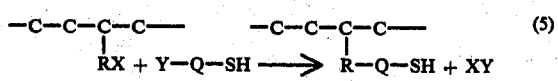
(5)

where X is an electropositive or electronegative atom or group, Y is respectively negative or positive, R is an organic group, particularly a carboxylic group, which cannot exist when X is electronegative, while Q represents another organic group which includes a carboxyl when Y is electropositive. As will be understood, the chain:

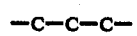

diagrammatically represents a macromolecule, without attempting to indicate its particular structure nor the number of lateral RX groups.

To illustrate this definition, two non-limitative examples are given of reactions according to the invention.

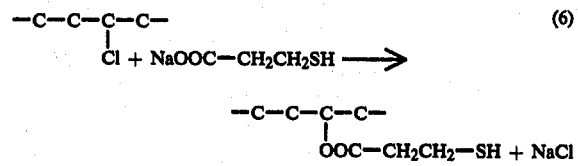
(6)

The reaction (6) corresponds in particular to the attachment of mercapto-propionic groups on the chain of a polyvinyl chloride.

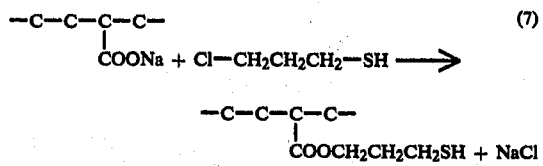
(7)

The latter reaction can correspond, for example, to the attachment of 1-mercapto-4-butyric groups on the chain of an acrylic or methacrylic polymer. This is also the case with polymers or copolymers of acrylic or methacrylic acid combined with an alkaline base.

Thus the invention allows the preparation of novel polymercaptans which can include the groups:

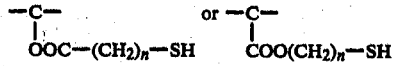

where n can range from 1 to 30, on the chain of a polymer.

In a particular embodiment of the invention, the process is carried out in such a manner that the group carrying the mercapto function is attached to a carbon atom in the alpha position to another carbon atom carrying a hydroxyl substituent. The presence of the —OH, thus located in the alpha position to the group carrying the —SH, can affect the solubility of the product in water and in organic solvents. At the same time, it also makes possible modifications of the hydrophilic-lipophilic balance of the product in the desired manner.

This embodiment can be carried out with polymers containing epoxy groups which are first opened by means of a reactant capable of attaching an electronegative atom or group, for example halogen, sulpho, dithiophosphoric or other, to the polymer and then treating the derivative obtained by a mercaptocarboxylate of a mineral or organic cation. Polymers which are particularly suitable for such a reaction are alkyl polyacrylates or polymethacrylates with epoxy groups. In practice, it is advantageous to employ copolymers of methyl, ethyl or other alkyl acrylates or methacrylates with glycidyl acrylates or methacrylates or glycidyl homologues.

By way of example, the formula (8) is given of a unit of a 50/50 copolymer of methyl methacrylate with glycidyl methacrylate:

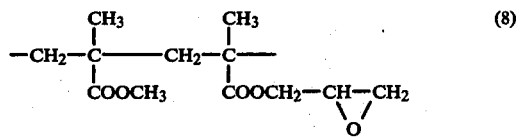

By the action of an appropriate reactant, particularly aqueous HCl, the epoxide bridge is opened to give the group:

In accordance with the invention, the polymer thus treated is then reacted with the mercaptocarboxylate of an organic or inorganic base, for example sodium mercaptopropionate, SH—CH$_2$CH$_2$COONa, which leads to the elimination of NaCl and the transformation of the groups (9) into:

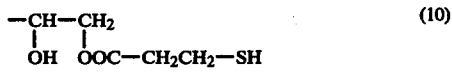

The process according to the invention can be carried out at variable temperatures, preferably ranging from 20° to 100° C., in an appropriate solvent. The duration of the reaction naturally depends upon the nature of the reactants and the temperature; it is usually in the range from 5 to 30 hours. During preparation and storage of the product, precautions are taken to avoid all contact with the air, because thiol polymers are very sensitive to the action of oxygen.

In the example of the formulae (8) to (10) above, a copolymer with one mole of methyl methacrylate, which does not take part in the reaction, has reacted with one mole of glycidyl methacrylate, the epoxy group of which reacts with the mercaptocarboxylate utilized. However, depending upon the properties sought, in particular according to the number of —SH functions which are desired to introduce into the macromolecule, copolymers containing variable proportions of glycidyl methacrylate with respect to the methyl methacrylate are employed. On the other hand, for a given copolymer, the proportion of the epoxide bridges opened can be varied and also the proportion of mercaptocarboxylate correspondingly utilized.

The invention is illustrated by the non-limitative Examples which follow.

EXAMPLE 1

Attachment of cinnamic groups to the copolymer of methyl methacrylate with glycidyl methacrylate.

The polymer utilized results from the copolymerization of one mole of methyl methacrylate with one mole of glycidyl methacrylate. Its molecular weight is 50,000 and its epoxy group content is 3.7 milli-equivalents per gram.

15 g of this copolymer was dissolved in 150 ml of distilled dimethyl-formamide containing 1.17 g water (130 m.eq.). To this solution, 10.2 g (0.0688 mole) of cinnamic acid, C$_6$H$_5$CH=CH—COOH, and 6.9 g (0.0681 mole) of triethylamine were added and the temperature was taken up to 80° C. The mixture was maintained at this temperature for 20 hours.

The reaction for opening the epoxide bridges of the polymer by cinnamic acid was monitored during the operation by ultraviolet spectrography. This confirmed with time a chage in the maximum absorption from the value of 267 nm to 276 nm, the latter value corresponding to that of the cinnamic ester formed.

When the reaction was completed, the product was slowly poured with agitation into 750 ml of sulphuric ether which gave rise to precipitation. The product was taken up in a minimum of dimethyl formamide and the solution obtained was again precipitated with ether. A very fine white powder was thus obtained, which is soluble in methanol and hot ethanol, but insoluble in water, glycerol, olive oil and soya oil.

Measurement of the epoxide residues indicated that the rate of opening of the latter exceeded 80%. U.V. analysis of the cinnamic ester, using methyl cinnamate as a reference, gave 48% for the proportion of epoxides opened by the cinnamic acid. It is thus possible to attribute the opening of 80−48=32% of the bridges to the hydrolysis reaction.

In order to open the remaining 20% of the epoxy groups, 10 g of the product obtained was dissolved in 50 ml of tetrahydrofuran (THF), to which was added 1.5 ml of aqueous HCl containing 0.457 g HCl (12.5 m.eq.). The mixture was allowed to stand at ambient temperature for 30 minutes, after which precipitation from ether was carried out. This purification was repeated by redissolving the precipitate in a minimum of THF, followed by a new addition of ether. The powder obtained, after drying, is soluble in methanol and in ethanol. It is insoluble in water and in glycerol.

EXAMPLE 2

Preparation of a powder insoluble in alcohol.

5 g of the very fine powder obtained in Example 1, still containing 20% of epoxides, that is to say not treated with HCl, was placed in 20 ml of sulphuric ether and 5 ml of 1,4-diaminobutane was added. The whole was heated under reflux with vigorous agitation for 3 hours. At the end of this reaction, the powder was washed several times with distilled water at 60° C. After drying, the powder, the grain size of which was of the order of microns, proved to be insoluble in ether, ethanol, water and glycerol. It is suitable for the preparation of anti-solar compositions based on solid particles.

EXAMPLE 3

The operations were the same as in Example 1, but the polymer solution contained a larger quantity of water. 20 g of glycidyl polymethacrylate of molecular weight 48,500 was dissolved in 190 ml of distilled dimethyl formamide containing 1.43 g water (160 m.eq.). 19.4 g of cinnamic acid and 13.2 g of trimethylamine were added to the solution. After 20 hours at 80° C., the solution was poured into 900 ml of ether. The polymer precipitated in a thick form which, after drying, yielded a fine powder. The remaining epoxide content of this powder was 17%, while 40% of the initial epoxide had been opened by the cinnamic acid, as indicated by U.V. measurement with, as a reference coefficient, methyl cinnamate. It can thus be seen that the remainder, that is to say $100 - (17 + 40) = 43\%$ of the initial bridges have been opened by hydrolysis. It can be seen that the increase in the water content of the diemthyl formamide used, with respect to Example 1, caused an increase in hydrolysis such that the product obtained became soluble in methanol, THF and hot ethanol. In glycerol, it is soluble at 70° C. at the rate of 80 g/l of glycerol. The latter solution does not precipitate when it returns to ambient temperature and the solution accepts unlimited quantities of water.

EXAMPLE 4

Stabilization of the product of Example 3.

10 g of the product prepared according to Example 3 was put into solution in 60 ml of THF and 1.46 g HCl or 40 m.eq. acid in the form of 38% aqueous HCl was then added. The reaction for opening 17% of the remaining epoxy bridges, in the product, was completed after 2 hours at ambient temperature. The polymer was then precipitated by the introduction of its solution into 300 ml of ether. After drying, the precipitate had the form of an extremely fine white powder.

It was confirmed that there were no longer any epoxy groups in this powder and that the 17% of residues, opened by the action of the HCl, were in the form of macromolecular chlorhydrins. The powder is soluble in the same solvents as the product of Example 3.

After two months of storage at ordinary temperature, this powder remained soluble and gave no sign of cross-linking commencing, in contrast to the product of Example 3, which was not sufficiently stable to be stored.

The efficacy of the powder of the present Example, from the standpoint of absorption of ultraviolet, was determined comparative with that of methyl cinnamate. In the 275-278 nm band, for a 27 mg/l methanolic solution of the powder, the same absorption was found as with a solution of 8.6 mg of methyl cinnamate per liter of methanol.

Measurement of the stability of the U.V. filter, effected comparatively with that of methyl cinnamate, showed that the two products evolve in the same fashion with time.

EXAMPLE 5

Fixation of cinnamic acid on a polymer in an anhydrous medium.

20 g of glycidyl polymethacrylate of molecular weight 48,500, having a polydispersity of 2.4, were dissolved in 190 g of anhydrous THF. To the solution so obtained, 19.4 g of cinnamic acid and 12.1 g of triethylamine were added, namely 93 moles of the acid and 85 moles of the amine per 100 moles of glycidyl methacrylate. The mixture was maintained for 20 hours at 60° C.

After precipitation of the polymer with ether and drying of the product, it was found in the latter that 84% of the epoxides had reacted. The content of cinnamic groups in the product, in solution in methanol, by U.V. at $\lambda = 278$ nm, with the coefficient of absorption of methyl cinnamate as reference, indicated a rate of 70% for epoxides having cinnamic groups attached. The product is soluble in THF and in methanol, but insoluble in ether, water and glycerol.

EXAMPLE 6

Suppression of the epoxides of the product of Example 5.

This operation was effected in two different ways on two separate portions of the product.

(1) 10 g of the product obtained according to Example 5 was dissolved in 100 ml of anhydrous THF and 50 m.eq. of HCl were added to the solution, in the form of the concentrated acid. The solution as allowed to stand for 30 minutes at about 30° to 40° C., after which the polymer was precipitated with ether and washed with the latter. At the end of this treatment, the epoxy bridges which subsist in the product of Example 5 were integrally transformed to chlorhydrins. The final product so obtained was soluble in THF and in methanol, but insoluble in ethanol.

(2) Another 10 g portion of the product of Example 5 was dissolved in 100 ml of dimethyl formamide and 18 ml of 0.73 N $H_2SO_4$ (or 13.2 m.eq. of acid) was added. The solution was heated to 80° C. for 15 hours. After cooling, the polymer was precipitated by the addition of ether.

By this operation, all the bridges which were not opened in Example 5 had undergone hydrolysis and replacement of the groups:

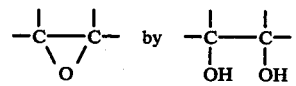

The resultant product, washed with ether and dried, is soluble in THF and methanol. It is insoluble in water and glycerol. It can be seen that hydrolysis (2), in place of chlorhydrination (1), rendered the product soluble in ethanol.

EXAMPLE 7

The preparation of Example 5 was repeated, but without the addition of triethylamine.

This confirmed that only 16% of the epoxide of the glycidyl polymethacrylate used had reacted. After measurement by U.V. at $\lambda = 278$ nm of the reaction product, 9% of the initial epoxides had retained cinnamic groups.

When treated with HCl, as in Example 6(1), to transform all the remaining epoxy bridges to chlorhydrin groups, the product became soluble in ethanol.

On the other hand, hydrolysis with 0.73 N $H_2SO_4$, with 6 H+ ions per 10 epoxy bridges, as in Example 6(2), led to a product soluble in water.

It can thus be seen that with more than 80% of the initial epoxides transformed into the groups:

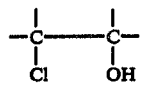

solubility in ethanol is obtained, while the same proportion of

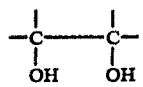

groups provides solubility in water.

EXAMPLE 8

Attachment of cinnamic groups to polyisobutene.

A polyisobutene of molecular weight 800 determined by tonometry, in the form of an oil having 2.1 unsaturated groups per 1000 g, was subjected to epoxidation with peracetic acid in well known manner.

The epoxided oil contained 1.15 epoxy groups per 1000 g. 5.3 g of trans-methoxycinnamic acid, $CH_3OC_6H_4CH=CHCOOH$, and 1.61 g of triethylamine were added to 20 g of this oil dissolved in 200 ml THF and then the mixture was maintained at 60° C. for 15 hours. Then, the solvent was removed under vacuum. After taking up the product in chloroform and washing with a solution of sodium bicarbonate and then with water to neutrality, the solution was dried and then the solvent was evaporated to separate the oily product formed. This showed that 80% of the epoxy bridges of the polyisobutene had been opened.

After treatment with 38% HCl in THF solution, as in the preceding examples, the product contained 1 methoxycinnamic group per 1200 g, viz about 15% by weight, or 1 group per 18 isobutene units.

The maximum absorption of light, determined for the product in a mixture of 75 parts hexane and 25 parts ethanol, was obtained with wavelengths of around 306 to 308 nm.

EXAMPLE 9

Attachment of trans-paramethoxy cinnamic acid to the polymer.

20 g of the same glycidyl polymethacrylate as in Example 5 were dissolved in 200 ml of anhydrous THF. To the solution obtained, which thus contained 130 m.eq. of epoxides, 130 m.eq. of trans-paramethoxycinnamic acid and 52 m.eq. of triethylamine were added. The mixture was maintained at 60° C. for 20 hours, after which the polymer was precipitated with ether and then dried. Analysis of the dried product indicated the attachment of methoxycinnamic acid to 90% of the initial epoxy groups of the polymethacrylate employed. This product is insoluble in water and in cold methanol, but dissolves in the latter in the hot.

In the manner described under (2) in Example 6, the product obtained was hydrolysed with aqueous $H_2SO_4$ in dimethylformamide. After this hydrolysis, the product became soluble in cold ethanol, but remained insoluble in water. It can thus be seen that attachment of 90% of p-methoxycinnamic acid groups to the polymer is too high for the formation of —OH groups, in place of the remaining epoxy groups, to be able to yield solubility in water.

EXAMPLE 10

The operations were the same as in Example 9, except that the proportion of catalyst, triethylamine, was reduced to a quarter, that is to say, it was reduced from 52 to 13 m.eq.

It was then found, after precipitation from ether and drying, that there was attachment of p-methoxycinnamic acid to 24% of the initial epoxy groups. The maximum absorption was located at 312 nm. The product was insoluble in water, but became soluble after sulphuric hydrolysis in aqueous medium, effected as in Example 9. Thus, solubility in water can be obtained by the creation of a larger number of hydroxyl groups than in Example 9.

EXAMPLE 11

Mercaptan modification of a polymer carrying methoxycinnamic groups.

In the manner described in Examples 9 and 10, a glycidyl polymethacrylate was prepared, having 22% of its epoxy groups opened by trans-paramethoxycinnamic acid. 20 g of this product of 86 m.eq. of epoxides was put into solution in 200 ml of tetrahydrofuran. 6.84 g, that is to say 90 m.eq., of propylmercaptan and 5.6 m.eq. of KOH dissolved in 7 ml of butanol were added. The mixture was heated to 60° C. for ½ hour. After cooling, 50 m.eq. of 38% aqueous HCl were added and, after ½ hour, the medium was neutralized with potash. The KCl formed was separated by filtration.

After precipitation of the polymer with ether, it was confirmed that virtually all the epoxide groups previously present adjacent the methoxycinnamic groups had been opened by the propylmercaptan. The sulphide functions thus attached can be transformed into sulphonium, sulphoxide or other sulphur-containing groups. They permit regulation of the solubility in water and other properties of the products.

EXAMPLE 12

Attachment of salicylic groups to a polymer.

In order to obtain an ultraviolet filter, salicylic acid was attached to glycidyl polymethacrylate, as in Example 5.

In order to avoid the action of the OH of the salicylic acid on the epoxy groups of the polymer and not to allow cross-linking to occur, operation was carried out so as to attach only a minor proportion of this acid. For this, $HO-C_6H_4-COOH$ was reacted with the polymer in the absence of a catalyst.

130 m.eq. of salicylic acid was reacted in 200 ml of tetrahydrofuran with 130 m.eq. of the epoxide in the form of glycidyl polymethacrylate. After 44 hours at 60° C., the mixture was treated with 1000 ml of sulphuric ether, which dissolved the remaining salicylic acid, while also precipitating the modified polymer. Washed and dried, the product still contained 75% of its initial epoxides, while 25% of them had attached salicylic acid to give groups:

In a 50/50 chloroform/methanol mixture, this product had a maximum absorption of light at a wavelength of 306 nm.

Hydrolysis.

Hydrolysis of 6.6 g of the modified polymer, obtained as indicated above, was effected with aqueous sulphuric acid in 60 ml of THF, with the molecular ratios: H+/epoxy=0.9 and H₂O/epoxy=73. The solution was heated to 60° C. for 40 hours. Precipitated with ether and dried, the hydrolysed product was soluble in water, methanol, ethanol and glycerol.

EXAMPLE 13

Attachment of a colourant material on a copolymer of vinyl-pyrrolidone with glycidyl methacrylate.

The copolymer utilized contained 95% weight of polyvinyl pyrrolidone. It was dissolved in dimethyl formamide. The colourant was Naphthol Yellow:

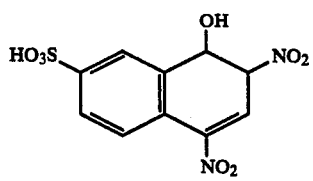

3 moles of this colourant were employed per mole of methacrylate, that is to say per epoxy group present in the polymer. The mixture was heated to 70° C. for 5 hours, after which the polymer was precipitated by introduction of the solution into heptane. The precipitate was yellow. It was suitable as a pigment for cosmetological utilization and had no toxicity.

Similar properties were obtained with eosinic and azinic colourants.

EXAMPLE 14

Attachment of a diazoic colourant.

To 6 g of the copolymer comprising 44 mole percent of methyl methacrylate and 56 mole percent of glycidyl methacrylate, molecular weight 50,000, dissolved in 100 ml of dimethyl formamide, 4.63 g of colourant 491/CB/I (commercial denomination) of the formula:

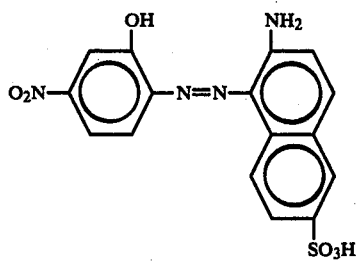

was added. The mixture was heated to 70° C. for 9 hours. After cooling, 2.9 ml of a 38% aqueous solution of HCl was added and the mixture was allowed to stand at ambient temperature for ½ hour. By precipitation from water, a very fine reddish-violet powder was obtained. The excess of the colourant was extracted by soxhlet apparatus by means of water. The polymer so obtained contained 9.6% of the initial colourant. In methanol, this product has an absorption of light at λ=525 nm, as against 500 nm for the initial colourant. The polymer thus coloured is insoluble in water. In acetone, it gives an excellent nail varnish.

EXAMPLE 15

Attachment of a colourant to a copolymer.

The copolymer is that of methyl methacrylate with glycidyl methacrylate, as mentioned in Example 14. 5 g (or 18.6 m.eq. of epoxide) was dissolved in 30 ml of dimethyl formamide. Also, 50 ml of a solution in the same solvent of 4.29 g of Sulphacide Yellow 5 R.L. light, of the formula:

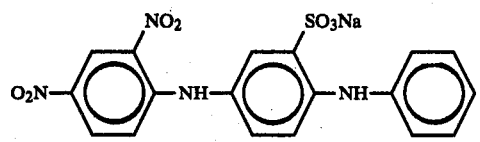

was prepared. The two solutions were combined and the mixture was heated without agitation for 24 hours at 70° C.

The final product was isolated by precipitation from water. A series of washings with distilled water eliminated the greater part of the colourant which was not combined with the polymer. These washings were each effected at 70° C. for 45 minutes. After purification completed by methanolic soxhlet extraction, 12 9 g of the colourant was found to be fixed per 100 g of product. Measurement was effected at 370 nm.

EXAMPLE 16

The polymer employed was a copolymer of 1 mole of methyl methacrylate with 1 mole of glycidyl methacrylate. Its molecular weight was 60,000 and its content of epoxide groups was 3.8 m.eq. per gram of product.

In a reactor, 35 g of this copolymer, that is 133 m.eq. of epoxide, was dissolved in 300 ml of distilled nitrogen-degassed dimethyl formamide. 1.5 times the stoichiometric proportion of concentrated HCl, viz. 13.4 g of a 38% aqueous solution of HCl, was added. The mixture was allowed to stand at ambient temperature for 1 hour. The epoxides were thus transformed into chlorhydrins.

A solution of 31 g of mercaptopropionic acid neutralized with caustic soda (292 m.eq. of this acid with 292 m.eq. of NaOH) in 50 ml of doubly-distilled nitrogen-degassed waer was then poured into the reactor. The temperature of this mixture in the reactor was taken to 75° C. and maintained at this value for 24 hours, with an energetic input of nitrogen.

At the end of the reaction, the product was poured into degassed water, well deprived of oxygen, which had the effect of precipitating the polymercaptan formed. This precipitate was washed with water to effect elimination of the excess carboxylate and the NaCl formed. Drying of the precipitate was effected at 45° C. under 1 mm of Hg for 24 hours. The product so obtained was totally soluble in tetrahydrofuran, which proved that it is free from cross-linking. Its structure by statistical distribution corresponds to the formula:

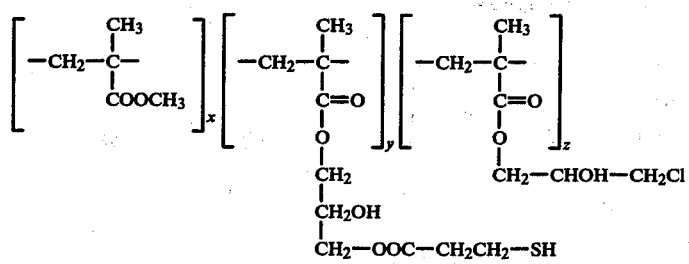

(11)

in which y, i.e. the thiol function units, constitutes 24 molar percent of the whole. The product is stored under nitrogen, preferably in the cold and in the absence of light.

EXAMPLE 17

As in Example 16, 35 g of the same copolymer dissolved in 300 ml of tetrahydrofuran was used. 160 m.eq. of chloracetic acid and 100 m.eq. of triethylamine were added to it and then the mixture was heated to 60° C. for 30 hours. The solution was then cooled to 20° C. and 200 m.eq. of HCl were added in the form of a 38% aqueous solution. After ½ hour, the mixture was poured into water, where it precipitated and was then washed and dried. The precipitate of the polymer was redissolved in 300 ml of distilled nitrogen-degassed dimethyl formamide. To the solution obtained, 50 ml of doubly-distilled water containing 292 m.eq. of sodium mercaptopropionate were added. The whole was heated to 75° C. for 24 hours. The product was then treated as in Example 1. In addition to the monomeric units of Example 16, the unit below was then found in the polymer:

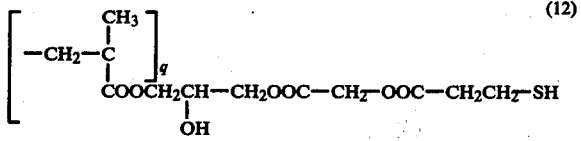

(12)

The sum of the units carrying an —SH function, i.e. the sum of y+q, is 34 molar percent, while the sum of the unreacted chlorinated units was 12 molar percent.

EXAMPLE 18

The starting polymer was polyvinyl chloride. 2 g of this polymer was dissolved in 50 ml of deoxygenated dimethyl formamide. To this solution 1.34 g of sodium mercaptopropionate dissolved in 15 ml of deoxygenated absolute methanol was added, the mixture being maintained at 70° C. for 22 hours.

At the end of this time, the modified polymer was recovered by precipitation from water under nitrogen atmosphere. It was purified by washing with water and then with methanol. The product obtained contained 0.7 m.eq. SH per gram.

A 50 g/l solution of this polymer in tetrahydrofuran gelled when oxygenated water was added. This confirmation was carried out by adding 1 ml of 2-vol. oxygenated water to 5 ml of the solution.

Gelification can also be produced by the addition of a solution of iodine in dimethyl formamide.

EXAMPLES 19 TO 23

Polymers were prepared in the manner described in Example 16, but with variable proportions of sodium mercaptopropionate at different temperatures and durations. The table below indicates the final compositions in the units x, y and z of the formula (11), as a function of the factors indicated. The second column gives the number of millimoles of units of chlorinated monomeric groups z, while the third column gives the corresponding number of millimoles of mercaptopropionate used.

TABLE

| Ex. No. | m. moles z | m. moles mer-captopropio-nate | °C. | Time h | Final Composition molar % | | |
|---|---|---|---|---|---|---|---|
| | | | | | x | z | y |
| 19 | 3.5 | 3.5 | 40 | 20 | 51.8 | 44.1 | 4.0 |
| 20 | 3.5 | 7.0 | " | " | 51.9 | 40.8 | 7.3 |
| 21 | 7.0 | " | 60 | " | 51.8 | 42.0 | 6.2 |
| 22 | 3.6 | 3.6 | 80 | 22 | " | 29.6 | 18.6 |
| 23 | 7.2 | " | " | 24 | 51.9 | 37.0 | 11.1 |

It can be seen that the process according to the invention allows regulation as desired of the proportion of units with —SH groups in the final polymer.

EXAMPLE 24

Application of the product obtained according to Example 16 to the elimination of heavy metals.

To an aqueous solution containing 1 mg of each of the cations of $Cu^{++}$, $Ni^{++}$ and $Cr^{+++}$ per liter, there was adder per liter 10 mg of the polymercaptan prepared according to Example 1, in the form of a 10% solution in tetrahydrofuran. After 2 hours of contact in the solution, filtered using active carbon, the remaining traces of these cations were measured by atomic absorption spectrophotometry.

There were then found: $Cu^{++}$: less than 0.01 mg/l, $Ni^{++}$: 0.02 mg/l and $Cr^{+++}$: less than 0.01 mg/l.

It is thus seen that the complexing of the three heavy metals by the polymercaptan according to the invention allows elimination of more than 99% of the copper and the chromium, as well as 98% of the nickel.

We claim:

1. A process of preparing an organic polymer having a chain carrying at least one active group attached to a chain carbon atom by chemical bonds comprising reacting a polymer having at least two epoxy bridges selected from the group consisting of polyolefin and a polymer or copolymer of an acrylate or methacrylate with an active group containing cosmetological compound selected from the group consisting of cinnamic acid, methoxycinnamic acid and salicylic acid such that 16–90% of the epoxy bridges are opened and one of each pair of the resulting epoxy carbon atoms has the active group cosmetological moiety bonded thereto and the other of the resulting carbon atoms carries a hydroxyl group, and thereafter opening the remaining epoxy bridges such that one of each pair of the newly opened epoxy carbon atoms carries a hydroxyl group and the other carries a halogen, hydroxy, amine or mercaptan group.

2. The process of claim 1 in which the reaction of the active group containing compound is effected in the presence of an organic base.

3. The process of claim 2 in which the organic base is a triamine.

4. The process of claim 3 in which the triamine is trimethylamine or triethylamine.

5. The process of claim 1 wherein said reactions are carried out in a solvent for the epoxidized polyolefin.

6. The process of claim 5 in which the solvent is dimethylformamide or tetrahydrofuran.

7. The process of claim 5 in which the solvent contains water.

8. The process of claim 1 in which the reaction with the active group containing compound is carried out at 60°–80° C. for 5–44 hours.

9. The process of claim 1 in which the polymer is a polymer or copolymer of an acrylate or methacrylate.

10. The process of claim 1 wherein said polymer is selected from the group consisting of glycidyl polymethacrylate, methyl methacrylate-glycidyl methacrylate copolymer and epoxidized polyisobutene.

11. The process of claim 1 in which said remaining epoxy bridges are opened by hydrolysis.

12. The process of claim 1 in which the remaining epoxy bridges are opened by contact with a concentrated aqueous solution of a halogen acid at a temperature of ambient to 40° C.

13. The process of claim 12 in which the resulting halohydrin groups are reacted with a mercapto carboxylate so as to substitute a mercapto group for the halogen.

14. The process of claim 1 in which the reaction of the active group containing compound is effected in the presence of a triamine and in water containing dimethylformamide or tetrahydrofuran solvent for the epoxidized polyolefin at 60°–80° C. for 5–44 hours and in which the polymer is selected from the group consisting of glycidyl polymethacrylate, methyl methacrylate-glycidyl methacrylate copolymer and epoxidized polyisobutene.

15. The process of claim 14 in which the remaining epoxy bridges are opened by contact with concentrated hydrochloric acid at a temperature of ambient to 40° C. whereby the remaining epoxy bridges open to form chlorohydrins and the product becomes insoluble in ethanol.

16. The process of claim 14 in which the remaining epoxy bridges are opened by contact with aqueous sulfuric acid whereby the remaining epoxy bridges open by hydrolysis and the product becomes soluble in ethanol.

17. The process of claim 14 in which the remaining epoxy bridges are opened by contact with 1,4-diaminobutane in ether whereby a diaminobutane moiety becomes carried by one of the pair of newly opened epoxy carbon atoms and the product becomes insoluble in ethanol.

18. The method of claim 14 in which the remaining epoxy bridges are opened by contact with propylmercaptan whereby a propylmercaptan moiety becomes carried by one of the pair of newly opened epoxy carbon atoms and a mercaptan modified cosmetological active polymer is obtained.

* * * * *